(12) United States Patent
Ayers et al.

(10) Patent No.: US 10,118,827 B2
(45) Date of Patent: Nov. 6, 2018

(54) COMBUSTION SYNTHESIS OF CALCIUM PHOSPHATE CONSTRUCTS AND POWDERS DOPED WITH ATOMS, MOLECULES, IONS, OR COMPOUNDS

(71) Applicants: Reed A. Ayers, Golden, CO (US); Nina L. Vollmer, Lakewood, CO (US)

(72) Inventors: Reed A. Ayers, Golden, CO (US); Nina L. Vollmer, Lakewood, CO (US)

( * ) Notice: Subject to any disclaimer, the term of this patent is extended or adjusted under 35 U.S.C. 154(b) by 887 days.

(21) Appl. No.: 14/275,641

(22) Filed: May 12, 2014

(65) Prior Publication Data

US 2014/0335197 A1 Nov. 13, 2014

Related U.S. Application Data

(60) Provisional application No. 61/822,073, filed on May 10, 2013, provisional application No. 61/927,400, filed on Jan. 14, 2014.

(51) Int. Cl.
| | | |
|---|---|---|
| A61K 35/32 | (2015.01) | |
| C01B 25/32 | (2006.01) | |
| A61L 27/12 | (2006.01) | |
| A61L 27/54 | (2006.01) | |
| B01D 39/20 | (2006.01) | |

(52) U.S. Cl.
CPC .............. *C01B 25/32* (2013.01); *A61L 27/12* (2013.01); *A61L 27/54* (2013.01); *B01D 39/2068* (2013.01); *A61L 2300/102* (2013.01); *A61L 2300/104* (2013.01); *A61L 2430/02* (2013.01)

(58) Field of Classification Search
None
See application file for complete search history.

(56) References Cited

U.S. PATENT DOCUMENTS

| | | | |
|---|---|---|---|
| 4,673,355 | A | 6/1987 | Farris et al. |
| 5,156,697 | A | 10/1992 | Bourell et al. |
| 5,188,678 | A | 2/1993 | Sekhar et al. |
| 5,382,405 | A | 1/1995 | Lowrance et al. |
| 5,490,969 | A | 2/1996 | Bewlay et al. |
| 5,607,474 | A | 3/1997 | Athanasiou et al. |
| 5,769,884 | A | 6/1998 | Solovay |
| 5,986,169 | A | 11/1999 | Gjunter |
| 6,019,936 | A | 2/2000 | Chung et al. |

(Continued)

FOREIGN PATENT DOCUMENTS

| | | |
|---|---|---|
| WO | WO 99/34845 | 7/1999 |
| WO | WO 01/23013 | 4/2001 |

OTHER PUBLICATIONS

Castillo et al. "Effects of Gravity on Combustion Synthesis of Functionally Graded Materials," Advances in Space Research, Jul. 2003, vol. 32, No. 2, pp. 265-270.

(Continued)

*Primary Examiner* — Chris R Tate
*Assistant Examiner* — Douglas F White
(74) *Attorney, Agent, or Firm* — Sheridan Ross P.C.

(57) ABSTRACT

The invention relates to a synthetic bone material and a process for making the same. The synthetic bone material may comprise multiple phases of calcium phosphate. Another aspect of the invention is a porous filter, and the method of making the same, and wherein the porous filter is substantially similar to the process for forming the synthetic bone material.

20 Claims, 15 Drawing Sheets

(56) References Cited

U.S. PATENT DOCUMENTS

| | | | |
|---|---|---|---|
| 6,090,732 | A | 7/2000 | Ito et al. |
| 6,136,029 | A * | 10/2000 | Johnson .................... A61F 2/28 |
| | | | 427/2.27 |
| 6,283,997 | B1 | 9/2001 | Garg et al. |
| 6,316,091 | B1 | 11/2001 | Richart et al. |
| 6,365,149 | B2 | 4/2002 | Vyakarnam et al. |
| 6,375,877 | B2 | 4/2002 | Lauf et al. |
| 6,458,162 | B1 | 10/2002 | Koblish et al. |
| 7,037,867 | B2 | 5/2006 | Yu et al. |
| 8,545,786 | B2 | 10/2013 | Ayers et al. |
| 9,066,995 | B2 | 6/2015 | Buffer |
| 2001/0016353 | A1 | 8/2001 | Janas et al. |
| 2002/0125592 | A1 | 9/2002 | Schulman et al. |
| 2002/0140137 | A1 | 10/2002 | Sapieszko et al. |
| 2003/0069638 | A1 | 4/2003 | Barlow et al. |
| 2003/0108664 | A1 | 6/2003 | Kodas et al. |
| 2003/0138473 | A1 | 7/2003 | Koblish et al. |
| 2004/0091547 | A1 * | 5/2004 | Ben-Nissan ............ A61L 27/12 |
| | | | 424/602 |
| 2004/0151751 | A1 * | 8/2004 | Cooper ................. A61L 27/425 |
| | | | 424/423 |
| 2005/0142495 | A1 | 6/2005 | Van Heerden et al. |
| 2005/0163861 | A1 * | 7/2005 | Epple ...................... A61L 27/46 |
| | | | 424/549 |
| 2009/0068285 | A1 * | 3/2009 | LeGeros ................ A61K 33/06 |
| | | | 424/641 |
| 2010/0191346 | A1 * | 7/2010 | Bloor ................. A61L 27/3608 |
| | | | 623/23.63 |
| 2010/0193093 | A1 | 8/2010 | Coffey |
| 2012/0141596 | A1 * | 6/2012 | Lally ................... A61L 24/0063 |
| | | | 424/602 |
| 2014/0212320 | A1 | 7/2014 | Ayers |

OTHER PUBLICATIONS

Official Action for U.S. Appl. No. 14/168,901, dated Sep. 11, 2015 13 pages.
Official Action for U.S. Appl. No. 14/168,901, dated Mar. 21, 2016 10 pages.
Aruna et al., "Combustion synthesis and nanomaterials," Current Opinion in Solid State and Materials Science, 2008, vol. 12, pp. 44-50.
Bertolino et al., "Ignition Mechanism in Combustion Synthesis of Ti—Al and Ti—Ni Systems," Intermetallics, 2003, vol. 11(1), pp. 41-49.
Brailovski et al. "Review of Shape Memory Alloys Medical Applications," Bio-Medical of Materials and Engineering, 1996, vol. 6(4), pp. 291-298.
Cavagna et al., "Macroporous Calcium Phosphate Ceramic: A Prospective Study of 106 Cases in Lumbar Spinal Fusion," Journal of Long-Term Effects of Medical Implants, 1999, vol. 9(4), pp. 403-412.
Denissen et al., "Net-shaped hydroxyapatite implants for release of agents modulating periodontal-like tissues," J Periodont Res, 1997, vol. 32, pp. 40-46.
Jie-Cai et al., "In-situ combustion synthesis and densification of TiC—xNi cermets," Materials Science and Engineering, 2000, vol. A280, pp. 328-333.
Kim et al., "Catalytically Assisted Self-Propagating High-Temperature Synthesis of Tantalum Carbide Powders," J. Am. Ceram. Soc., 2001, vol. 84(5), pp. 976-982.
Kivrak et al., "Synthesis of Calcium Hydroxyapatite-Tricalcium Phosphate (HA-TCP) Composite Bioceramic Powders and Their Sintering Behaviour," J. Am. Ceram. Soc., 1998, vol. 81(9), pp. 2245-2252.
Koster et al., "Experimenteller Knochenersatz durch resorbierbare Calciumphosphat-Keramik" Translation: "Experimental Bone Replacement with Resorbable Calcium Phosphate Deramic," 1976, Langenbecks Archiv Fuuer Chirurgie, vol. 341, pp. 77-86.
Koster et al., "Resorbierbare Calciumphosphatkeramik im Tierexperiment unter Belastung," Langenbecks Arch. Chir., 1977, vol. 343, pp. 173-181.
Patil et al, "Combustion synthesis," Current Opinion in Solid State and Materials Science, 1997, vol. 2, pp. 158-165.
Taboas et al., "Indirect solid free form fabrication of local and global porous, biomimetic and composite 3D polymer-ceramic scaffolds," Biomaterials, 2003, vol. 24, pp. 181-194.
Tas et al., "An investigation of the chemical synthesis and high-temperature sintering behaviour of calcium hydroxyapatite (HA) and tricalcium phosphate (TCP) bioceramics," Journal of Materials Science: Materials in Medicine, 1997, vol. 8, pp. 91-96.
Tas, "Chemical Preparation of the Binary Compounds in the Calcia-Alumina System by Self-Propagating Combustion Synthesis," J. Am. Ceram. Soc., 1998, vol. 81(11), pp. 2853-2863.
Tas, "Combustion synthesis of calcium phosphate bioceramic powders," Journal of European Ceramic Society, 2000, vol. 20, pp. 2389-2394.
Yi et al., "Self Propagating High Temperature Synthesis of Powder-Compacted Materials," Journal of Materials Science, 1190, vol. 25(2), pp. 1159-1168.
Wong et al., "Functionally graded tricalcium phosphate/fluoroapatite composites," Materials Science and Engineering, 2002, vol. 20(102), pp. 111-115.
Zanotti et al. "Porous Ni—Ti ignition and combustion synthesis," Intermetallics, 2007, vol. 15(3), pp. 404-412.
Zhang et al., "Combustion Synthesis of Advanced Porous Materials in Microgravity Environment," Colorado School of Mines, 1999, retrieved from www.ncmt.org/events/combustion1999, 5 pages.
Official Action for U.S. Appl. No. 10/621,752, dated Jun. 15, 2009, 10 pages.
Official Action for U.S. Appl. No. 10/621,752, dated Dec. 22, 2011, 9 pages.
Official Action for U.S. Appl. No. 10/621,752, dated Nov. 10, 2011, 45 pages.
Notice of Allowance for U.S. Appl. No. 10/621,752, dated May 24, 2013, 8 pages.
Grossin et al., "Biomimetic apatite sintered at very low temperature by spark plasma sintering: Physico-chemistry and microstructure aspects," Acta Biornaterialia, 2010, vol. 6, pp. 577-585.
Kawagoe et al., "Preparation of Transparent Hydroxyapatite Ceramics by spark Plasma Sintering and Cell Culture Test," Phosphorous Res. Bulletin, 2006, vol. 20, pp. 119-128.
Lee et al., "Comparative Study for the Dissolution of bone Ash-derived and Artificial Hydroxyapatite," Adv. Materials Res., 2012, vols. 488-499, pp. 592-596.
Thitiset et al., "Development of Collagen/Demineralized Bone Powder Scaffolds and Periosteum-Derived Cells for Bone Tissue Engineering Application," Int. J. Mol. Sci., 2013, vol. 14, pp. 2056-2071.
Official Action for U.S. Appl. No. 14/168,901, dated Dec. 14, 2016 10 pages.
Official Action for U.S. Appl. No. 14/275,641, dated Mar. 13, 2017 11 pages Restriction Requirement.
Official Action for U.S. Appl. No. 14/275,641, dated Aug. 25, 2017 13 pages.
Official Action for U.S. Appl. No. 14/275,641, dated Dec. 18, 2017 15 pages.
Official Action for U.S. Appl. No. 14/275,641, dated Apr. 6, 2018 19 pages.
Official Action for U.S. Appl. No. 14/275,641, dated Aug. 8, 2018 22 pages.

* cited by examiner

COMBUSTION SYNTHESIS OF CALCIUM PHOSPHATE CONSTRUCTS AND POWDERS DOPED WITH ATOMS, MOLECULES, IONS, OR COMPOUNDS

CROSS-REFERENCE TO RELATED APPLICATIONS

This non-provisional patent application claims the benefit of priority from U.S. Provisional Patent Application No. 61/822,073 filed May 10, 2013, and U.S. Provisional Patent Application No. 61/927,400 filed Jan. 14, 2014, the entire disclosure of each is hereby incorporated by reference in their entirety.

GOVERNMENT LICENSE RIGHTS

This invention was made with government support under grant number 1R15AR060011-01, awarded by the National Institute of Health (NIH). The Government has certain rights in the invention.

TECHNICAL FIELD

This invention relates to generating calcium phosphate constructs and powders substituted with monovalent, divalent, trivalent or tetravalent atoms, molecules or ions, or chemical compounds using combustion synthesis, and the products produced therein.

BACKGROUND OF INVENTION

Serious body trauma caused by extensive battlefield injuries, such as that arising from high-velocity gunshot wounds, can lead to the loss of bone. In particular, battlefield activities can leave participants in need of having bones repaired by grafting. Autologous and cadaveric bone are considered the gold-standard bone graft materials. Their advantage is that they retain osteogenetic, osteoinductive, and osteoconductive properties that are required for bone regeneration. However, due to the nature of their harvesting, only a limited amount of bone tissue can be extracted. For autologous bone, detrimental side effects such as discomfort, donor site morbidity, secondary surgical procedures and risk of patient mortality or weakness resulting in fracture can occur. Allograft bone risks the transfer of antigens/disease, improper bone bonding, uncontrolled resorption and subsequent graft failure.

One specific area of interest is spinal fusion surgery, where it is estimated that more than 200,000 of these surgeries are performed each year in the United States alone, and this number continues to rise. Spinal fusion surgeries consist of removing an intervertebral disc and fusing the adjoining vertebrae. Current surgery implants include autografts and allografts. An additional surgery to remove bone from the iliac crest of the pelvic girdle is required for autografts. Its use has the significant advantage of reduced rejection by the patient. But many patients experience discomfort or donor site morbidity as a result of the extra procedure, while others may not have enough bone available for removal. Risks associated with allografts include disease transmission, supply limitations, and poor natural bone growth, or uncontrolled re-sorption after fusion surgery. At its optimum, a graft should be resorbed in such a manner that it allows sufficient time and structure for vascularization of the porosities and subsequent bone ingrowth.

There is significant demand for large scale, bioresorbable, biocompatible, and bioactive bone graft substitute materials (BGSM). Synthetic calcium phosphates represent an option for BGSM. Currently available synthetic calcium phosphate bone graft materials are limited to specific chemistries of calcium and phosphate due to the nature of their manufacturing processes (wet chemistry precipitation, sol-gel, sintering, ashing of bovine or human bone). In reality, the mineral phase of bone has a complex chemistry, in addition to significant mechanical, biological and material properties.

Currently available synthetic calcium phosphate bone graft materials are limited to specific chemistries of calcium and phosphate due to the nature of their manufacturing processes. Two main methods are currently used to produce synthetic calcium phosphate bone graft materials. Some methods are wet methods, such as aqueous precipitation, gel casting, slurry dipping, spraying, sol-gel processes, or hydrolysis of calcium phosphates. A disadvantage of wet methods is that it can take weeks to produce small quantities of product. The second method utilizes solid-state reactions, which include uniaxial or isostatic compaction of loose powders, followed by a heat treatment. Other solid-state reactions include hot pressing, 3-dimensional laser printing and selective laser sintering. Solid-state reactions require high production time, cost and labor for bulk production and require multiple heat treatments to produce.

In addition to the need for bone graft materials, there is also a need for those BGSM to be resistant to microbial growth. Postoperative infections caused by gram positive bacteria (e.g. *S. aureus, S. epidermidis, Streptococcus* spp.) are one of the biggest challenges in battlefield orthopedic surgery. Incorporation of a localized antibiotic component, such as ionic sliver, within the implant could reduce the incidence of infection. Ionic silver is considered to have a broad spectrum of antimicrobial properties at concentrations as low as about 35 ppb without toxic effects to mammalian cells. It has been shown that silver (Ag) ions and Ag-based composites are highly toxic to microorganisms and incorporation of an antimicrobial component, for example silver based antimicrobial components, in the BGSM could create a localized antibiotic effect.

What is needed is a self-propagating reaction process that would provide the ability to synthesize calcium phosphate materials that could be incorporated into bone, bone grafts, or used as a filter. Ideally, the chemistry of the calcium phosphates could be tailored to suit the type of bone that is being grafted. Furthermore, it would be ideal if dopants, such as antimicrobial agents or materials that alter the BGSM properties, could be combined in the synthesis process and incorporated into the final product. Finally, it would be desirable to develop a process that would produce materials to deliver a controlled dose of an antimicrobial agent over time.

SUMMARY

Considerable research has gone into reducing the energy input and time consumption involved in materials manufacturing. One attractive approach is to form chemical materials using self-sustaining, or self-propagating reactions, wherein the heat of formation of the products drives the reaction to completion, i.e. to the right. Several chemical approaches that utilize self-propagating reactions include combustion synthesis (CS), self-propagating high-temperature synthesis (SHS), and rapid solid-state metathesis reactions (SSM). An example of an energetic self-propagating reaction is the SSM reaction between $GaI_3$ with $Li_3N$ to produce GaN shown in Eq. 1:

$$GaI_3 + Li_3N \rightarrow GaN + 3LiI \quad (1)$$

The driving force of this reaction is $\Delta H_{rxn}$ of −515 kJ, which is four times as energetic as the elemental reaction shown in Eq. 2:

$$Ga + 0.5N_2 \rightarrow GaN \quad (2)$$

where the enthalpy of the reaction, $\Delta H_{rxn}$, is about −110 kJ. The key aspects of these reactions are that they are self-propagating, and that they require an external energy source to initiate, or ignite the reaction.

SHS, like SSM reactions, is a process that utilizes the exothermic properties found in the synthesis of many compounds to create a self-sustaining reaction. The process takes advantage of the exothermic nature of the reactions and offers users benefits including high purity of product, lower energy and material costs and reduced overall time of manufacturing. SHS products can be tailored with specific amounts of porosity, and because of the reactions unique thermodynamics and kinetics, a number of advantageous intermediate, nonstoichiometric products are possible.

Many different types of materials have been prepared using SHS processes. An example of an SHS reaction is the so-called thermite reaction, wherein a metal and a metal oxide undergo a highly exothermic oxidation/reduction reaction that produces tremendous heat. For example, the reaction between iron oxide and aluminum given in Eq. 3:

$$Fe_2O_3 + 2Al \rightarrow 2Fe + Al_2O_3 \quad (3)$$

The highly reactive nature of aluminum drives the reaction to the right by aluminum oxidation and iron reduction. While this reaction will burn brightly and generate much heat, it does not require external oxygen and can, therefore, proceed in locations with limited air flow, or even under water.

Even though a self-propagating reaction is exothermic, in order for the reaction to become self-sustaining, sufficient energy must be present during the initiation process for a small portion of the reactants to convert to the desired product. This is known as initiation. Once the reaction is initiated in a local region, an energetic reaction wave proceeds through the remaining mass of reactants.

The invention takes advantage of self-propagating reactions to form a synthetic calcium phosphate material. The chemical reactant powders used to produce the synthetic calcium phosphate materials may comprise calcium oxide (CaO) and phosphorus oxide ($P_2O_5$), and optionally a third component, wherein the third component may be an atom, an ion, molecule, or a compound. In particular, the third component may be an antimicrobial agent. The third component may be a metal atom, ion, molecule or compound such as silver, gold, copper, zinc or silver nitrate.

This invention can produce implant materials for patients with reduced capacity to form new bone. An advantage of the invention over the prior art is that the synthetic bone graft material can include elements or molecules that can stimulate biologic activity. Dopants such as magnesium, strontium and tin can be used. Magnesium stimulates collagen synthesis in the osteoblast and can improve adhesion and bioactivity, while strontium can reduce osteoblast activity (an anti-osteoprosis agent). Tin has a slight anti-inflammatory effect on cells, helping mediate the healing process.

Additionally, no synthesis process currently exists that can selectively include cations in the CaP structure at a controlled level.

One aspect of the invention is a method of producing a synthetic bone graft material, comprising mixing calcium oxide and phosphorus pentoxide to form a mixture, and providing an ignition source to the mixture in an inert atmosphere to form the synthetic bone graft material.

Another aspect of the invention is a bone graft material, which includes calcium orthophosphates. Unlike prior art bone graft materials where the material is in a homogeneous phase, the invention can be made with multiple phases rather than a homogenous phase. Thus, in some embodiments, calcium phosphates include multiple phase, such as hydroxyapatite, and tricalcium phosphate. The tricalcium phosphate may be α-tricalcium phosphate and/or β-tricalcium phosphate. Hydroxyapatite and tricalcium phosphate are members of the calcium orthophosphate family and used to describe specific atomic ratios of calcium and phosphate (i.e. hydroxyapatite—5:2, and tricalcium phosphate—3:1).

In still other embodiments, a dopant can be incorporated into the bone graft.

Another aspect of the invention is a synthetic porous filter, including calcium phosphate, wherein the calcium phosphate is formed by mixing calcium oxide and phosphorus pentoxide to form a mixture, and providing an ignition source to the mixture in an inert atmosphere to form the porous filter.

Another aspect of the invention is a synthetic bone manufactured using a cost-effective manufacturing method (combustion synthesis) that rapidly creates calcium phosphate materials that can closely mimic the chemistry, mechanical and biological properties of the mineral phase of bone. Additionally, this technique can enhance, improve or incorporate specific properties into the synthesized calcium phosphate materials furthering their biologic potential. Once synthesized, the CaP scaffolds can be infiltrated with biologic or other proteins/polymers that both act as bioactive components and reinforcing agents and toughen the overall construct based on "tuning" the CaP surface chemistry and active regions in the proteins/polymers. Additional applications of this technology include the synthesis of filter systems, and scaffolds for tissue ex-vivo reconstruction.

Yet another aspect of the invention produces a composite protein/polymer calcium phosphate material that more closely mimics the chemistry, mechanical, biological and material properties of bone. Additionally, this process can enhance, improve or incorporate specific properties into the synthesized calcium phosphate materials. This invention utilizes the extremely reactive, exothermic nature of the calcium oxide-phosphorous pentoxide reaction. The addition of metallic or other constituents can be accomplished by including the appropriate weight or atomic percentage of the component to the reactants (provided they can withstand the reaction temperatures).

Another aspect of the invention is a calcium phosphate ceramic products consisting of α-TCP and β-TCP. The tricalcium phosphate products exhibit excellent biomimetic properties, making them a suitable option for synthetic bone replacement material. Tricalcium phosphate constructs can be prepared by pressing powders and performing combustion synthesis reactions and with post synthesis heat treatments.

One aspect of the invention is a method of producing a synthetic bone graft material, comprising calcium oxide and phosphorus pentoxide to form a mixture, and providing an ignition source to the mixture in an inert atmosphere to form the synthetic bone graft material.

Another aspect of the invention is a synthetic bone graft material, comprised of calcium phosphate, and an antimicrobial agent.

Yet another aspect of the invention is a synthetic porous filter, comprising calcium phosphate, wherein the calcium phosphate can be formed by mixing calcium oxide and phosphorus pentoxide to form a mixture, providing an ignition source to the mixture in an inert atmosphere to form the porous filter.

DETAILED DESCRIPTION

Figure 1:
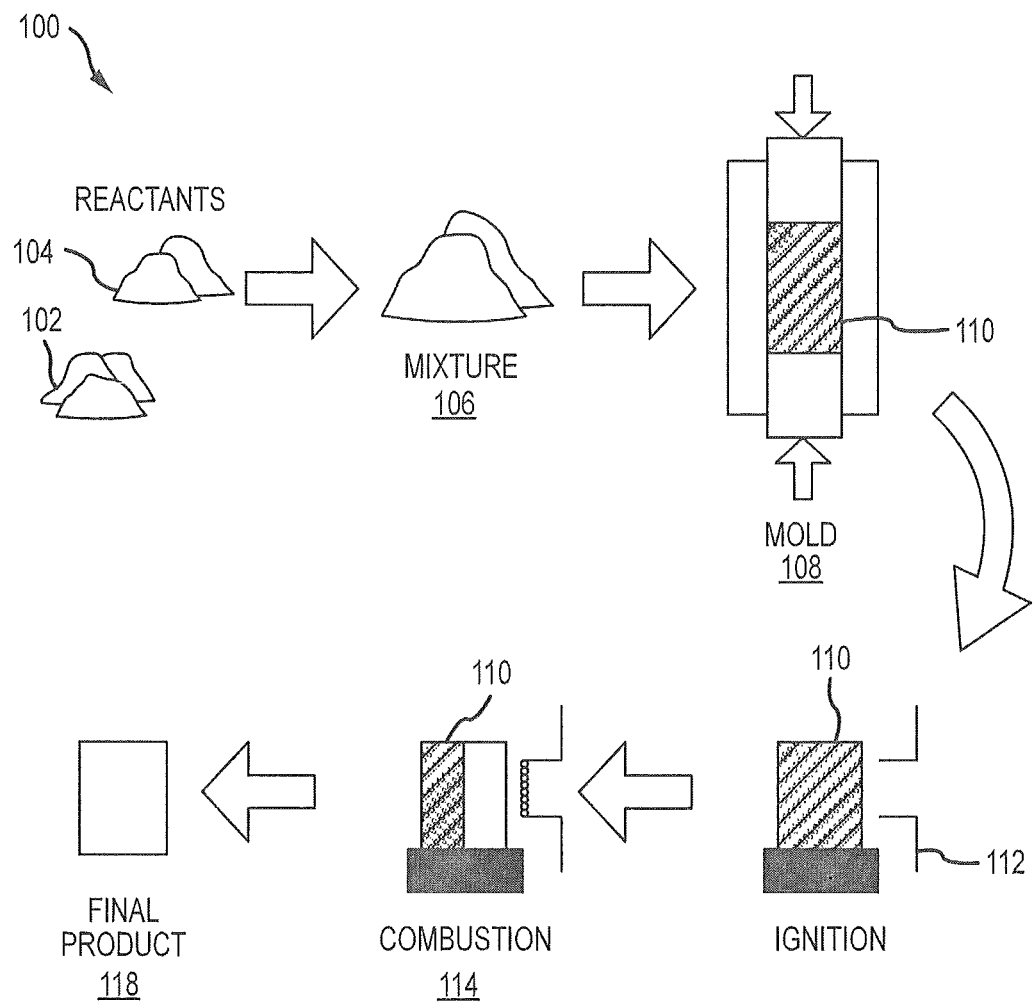
FIG. 1 illustrates a method for producing a synthetic bone graft material.

The invention is related to a synthetic calcium phosphate material for use in bone graft substitute materials, methods for using and methods for preparing the same. Calcium phosphates are also known as calcium orthophosphates, and are salts of orthophosphoric acid and can form compounds that contain $H_2SO_4^-$, $HPO_3^{2-}$, or $PO_4^{3-}$.

Definitions

By "chemical material," or "chemical reactant" it is intended to mean an element, a metal, an alloy, an oxide, a metalloid, or any other collection of elements or compounds that can be assembled, agglomerated, collected, pressed, or put together with other elements, metals, alloys, oxides, metalloids, or any other collection of elements or compounds.

By "coherent radiation" it is intended to mean the emission from one or more devices that emits light amplified stimulated emission of radiation. The emission is electromagnetic radiation and may be in the visible, ultra violet, or infrared portion of the electromagnetic spectrum, or in any combination of portions of the electromagnetic spectrum. The coherent radiation is notable for its high degree of spatial and temporal coherence. As used herein, the terms "coherent radiation," "laser light" and "laser emission" are synonymous.

By "initiation" it is intended to mean starting a reaction or process. As used herein, the terms "initiation" and "ignition" are synonymous.

By "laser" it is intended to mean a device that emits light amplified stimulated emission of radiation. A laser may emit electromagnetic radiation that is in the visible, ultra violet, or infrared portion of the electromagnetic spectrum. The radiation is notable for its high degree of spatial and temporal coherence. As used herein, the terms "laser" and "coherent radiation source" are synonymous.

By "optical fiber" it is intended to mean a flexible, transparent fiber made of glass (silica) or plastic, which may be only slightly thicker than a human hair. It functions as a waveguide, or light pipe to transmit light between the two ends of the fiber.

By "self-propagating" it is intended to mean a reaction that is exothermic, that consumes the available reactants, and that proceeds to completion once initiated. As used herein, the terms "self-propagating", "self-sustaining" and "combustion" are synonymous.

An aspect of the invention is a method of producing a synthetic bone graft material comprising mixing a calcium source with a phosphate source to form a mixture, and providing an ignition source to the mixture in an inert atmosphere to form the synthetic bone graft material. The calcium source may be any suitable material that allows for an exothermic, self-propagating reaction with the phosphate source, which likewise, may be any suitable material that allows for an exothermic, self-propagating reaction with the calcium source. Suitable calcium sources include, but are not limited to, calcium oxide, calcium carbonate, calcium hydroxide, calcium fluoride, calcium nitrate, or combinations thereof. Suitable phosphate sources include, but are not limited to, phosphorous pentoxide, phosphate ($PO_4^{3-}$), pyrophosphate, compounds thereof, and combinations thereof.

In an embodiment of the invention, the method to synthesize bone graft substitute materials may use a self-propagating chemical reaction, which comprises mixing the chemical reactants, and initiating the chemical reaction. Any suitable calcium source and phosphorous source may be used, and it is understood that the ratios discussed herein could be readily determined by one who has ordinary skill in the art. Calcium oxide and phosphorous pentoxide are illustrated as examples of the invention. Calcium oxide and phosphorous pentoxide can be mixed to prepare multiple calcium phosphate products. Equation 4 illustrates the chemical reaction for forming tricalcium phosphate, while Equation 5 illustrates the chemical reaction to prepare tetra-calcium phosphate product.

$$3CaO + P_2O_5 \rightarrow Ca_3(PO_4)_2 \qquad (4)$$

$$4CaO + P_2O_5 \rightarrow Ca_4P_2O_7 + O_2 \qquad (5)$$

The calcium oxide and phosphorus pentoxide may be mixed in air. These suitable reaction powders may be mixed and combusted in order to produce the calcium phosphate products. In an embodiment, the calcium oxide and phosphorus pentoxide may be mixed in a non-oxygen containing atmosphere, such as provided in a dry box or dry bag. Mixing may occur in air, a vacuum, a non-oxygen containing atmosphere, in an oxygen containing atmosphere, in an atmosphere comprising an inert gas, or a combination thereof. In some embodiments, the inert gas may be argon, helium, nitrogen, or any other gas that is largely free of oxygen and/or water vapor. In some embodiments, argon may be used as the inert gas.

The calcium oxide and the phosphorous pentoxide may be a commercially available powder, in any suitable size or purity. The ratio of the calcium oxide to phosphorus pentoxide may vary depending on the desired properties of the final product. In some embodiments, about 0.5 to about 0.6 parts of calcium oxide may be used for between about 0.4 to about 0.5 parts of phosphorous pentoxide. In some embodiments, the ratio of calcium oxide to phosphorous pentoxide may be about 0.54 to about 0.46. In some embodiments, a dopant may be used. Between about 0.005% by weight to about 30% by weight of the dopant may be used, however, any suitable amount of the dopant can be added so long as the reaction maintains the ability to self-propagate. The dopant may be an atom, an ion, a molecule, a compound or combinations thereof. The dopant may be added prior to mixing the calcium oxide and the phosphorous pentoxide, or may be added after the mixture is formed. In some embodiments, the molar ratio of the calcium oxide to phosphorous pentoxide to dopant may be about 3:1:0.29. In some embodiments, the dopant is an antimicrobial agent. The antimicrobial agent may be an atom, an ion, a molecule, or a compound. By way of non-limiting example, in some embodiments, the antimicrobial agent may be silver, gold, copper, zinc, silver nitrate or combinations thereof. In some embodiments, the antimicrobial agent may be silver (Ag) in the metallic or ion state. In some embodiments, the dopant can be strontium or SrO. Strontium may increase the compressive strength of the CaP material compared to TCP and HA scaffolds. In some embodiments, the dopant may be magnesium or MgO. Magnesium and strontium may increase bone formation, bioresorption and cellular activity of CaP scaffolds. The dopant can be used to affect the thermodynamics of the reaction system, increasing or decreasing the available enthalpy so that combustion temperature can be maintained at a temperature sufficient to generate a desired high temperature phase (HA, $\alpha$-TCP) or low temperature phase ($\beta$-TCP). In some embodiments, HA and/or TCP may be added to the mixture in order to increase the concentration of HA and/or TCP in the final product or to control the reaction properties or the product properties.

Any suitable method may be used to mix the calcium oxide, phosphorous pentoxide and, if used, dopant. By way of example, a vibrational mixer may be used. Other suitable alternatives would be understood by one skilled in the art when considering the reactant materials.

The mixture may be formed into a pellet before the ignition source may be used to form the synthetic bone graft material. The pellet formed may be any suitable shape or size. The shape and size of the pellet form may be chosen based on the intended application of the synthetic bone graft material. In some embodiments, the shape may be a cylinder, a cube, a sphere, an ovoid, a cuboid, an antiprism, a cupola, a hemisphere, a cone, a pyramid, a prism, or any other shape. The pellet may be formed at room temperature. In some embodiments, the pellet may be formed at a temperature less than the ignition temperature for the reaction system typically less than about 100° C. In some embodiments, the pellet can be formed at a temperature between about 25° C. and about 100° C. In some embodiments, the pellet can be formed at a temperature of about 25° C., about 30° C., about 35° C., about 40° C., about 45° C., about 50° C., about 55° C., about 60° C., about 65° C., about 70° C., about 75° C., about 80° C., about 85° C., about 90° C., about 95° C., or about 100° C. In some embodiments, the pellet may be formed in a press that may be cooled, such as a cold-press, may be operated at room temperature, or may be heated, as for a hot press. In some embodiments, the synthetic graft material may be a powder. The powder may be used in a putty or other suitable material. The powder may be formed by producing a pellet, then milled or crushed to form the powder. Alternatively, the powder may be formed directly from the mixture, which may be ignited to form the synthetic graft material. The force and time duration to form the pellet may be a function of the volume of the pellet. In some embodiments, the force applied to the mixture to form the pellet may be between about 1 psi to about 80 ksi. In some embodiments, the force may be applied for between about 1 seconds to the completion of the reaction, in some embodiments about 60 minutes. The force may be applied to all sides of a mold, a single side, two sides, or in less all of the sides of the mold. The force applied to the mold may result in a variable density of the pellet and/or final product.

The ignition source may be any suitable ignition source. In some embodiments, the ignition source may include, but is not limited to, a laser, a hot wire, an oven, a furnace, a flame, a torch, Joule heating, a hot press, a chemical catalyst, a chemical reaction and combinations thereof. By way of example, the mixture may be ignited when an ignition source is in physical contact with the pellet, or in close proximity to the pellet. The appropriate proximity may be determined through un-burdensome experimentation. The material of the ignition source may be any suitable material, for example, any metal or alloy. In some embodiments, the material of the ignition source may not react with the pellet mixture materials. In other embodiments, the material of the ignition source may be selected to be a metal or alloy that would be intentionally incorporated by the calcium phosphate products. In some embodiments, a laser may be used as the ignition source. The laser may operate in any suitable mode, including continuous wave or pulsed operation. The laser may fire in a pulsed fashion, wherein the pulses may be emitted between about 0.01 seconds to about 1.0 seconds. The power of the lasers coherent radiation pulses may vary between about 100 watts to about 2,000 watts. The laser may position the coherent radiation source and chemical reactants in such a way as to allow contacting of the chemical reactants by the coherent radiation, and contacting the chemical reactants with coherent radiation. The positioning may involve using lenses to focus the radiation and mirrors to position the focused radiation in a place that is not directly opposite the laser opening. The heat source may deliver the radiation through a fiber optic to the reactant powders. The laser may be a gas laser, a chemical laser, an excimer laser, a solid-state laser, a fiber laser, a photonic crystal laser, a semiconductor laser, a dye laser, a free electron laser, or a bio laser. The laser may be tunable, as it may be when the wavelength of the laser is variable. The wavelength may be varied between about 200 nm and about 1,500 nm.

In some embodiments, the ignition may occur in air, a vacuum, a non-oxygen containing atmosphere, in an oxygen containing atmosphere, or in an atmosphere comprising an inert gas, or a combination thereof. The inert gas may be selected from the group consisting of helium, argon, nitrogen, carbon dioxide, and combinations thereof. In some embodiments, argon may be used as the inert gas to create an inert atmosphere. Nitrogen and carbon dioxide have higher heat capacities than argon, affecting reaction thermodynamics by acting as a heat sink and also possibly reacting with the calcium (e.g. form carbonate apatite) while remaining non-toxic to tissues. In some embodiments, the combustion chamber pressure may remain at atmospheric pressure. Following the reaction, the product may be allowed to cool to room temperature in the combustion atmospheres. The cooling rate can be between about 100° C./min and about 10,000° C./min. The cooling rate allows for retention of metastable phases, for example tetra-calcium phosphate. In some embodiments, the cooling rate may be greater than about 200° C./min. In some embodiments, the cooling rate may be about 100° C./min, about 200° C./min, about 250° C./min, about 500° C./min, about 750° C./min, about 900° C./min, about 5,000° C./min, about 7,500° C./min, or about 10,000° C./min.

Some embodiments can include a heat treatment. Heat treatment temperatures can be selected using the CaO—$P_2O_5$ phase diagram. Different phases can be used to vary phase compositions and properties and hence subsequent solubility, toughness and protein/polymer binding. In some embodiments, the heat treatment can be at a temperature between about 25° C. to about 1300° C. In some embodiments, the heat treatment temperature can be between about 1100° C. to about 1250° C. In some embodiments, the heat treatment temperature can be at about 1100° C., about 1150° C., about 1200° C. or about 1250° C. It would be understood by one skilled in the art that the duration of the heat treatment would be a function of the volume being treated and can be determined without burdensome experimentation. Thus, the heat treatment can occur for any required time period. In some embodiments, the heat treatment can occur for between about 30 minutes to about 24 hours. In some embodiments, the heat treatment can occur for about 30 minutes, about one hour, about 90 minutes, about 120 minutes, and any time necessary up to about 24 hours. Following the heat treatment, the product can cool to room temperature.

An additive material can be combined with the CaP products. The additive material can be added following the heat treatment or may be added to products that have not been heat treated. The additive material can be collagen, immunofluorescence label, alginate, chitosan coatings, BMPs, VEGF, allograft or xenograft bone or tissue or other proteins or mixtures thereof. Products can be treated, under a sterilized and ventilated environment. The prepared protein solution can be added to submerge the products in the protein solution, where the products can remain for between about 2 hours to about 72 hours, in some embodiments up to about 72 hours. The products submerged in the protein solution can be agitated for some or part this time. Following the agitation, the sample can be removed from the solution. The products can be rinsed with phosphate buffered saline, hanks balanced salt solution, micropure, nano pure, tissue culture, distilled or deionized water or any other routinely used rinsing solvent. The products can then be dried at room temperature for between about 2 hours to about 48 hours. The process of submerging and drying can be repeated multiple times and the products can be coated with multiple materials (using a different coating material for each application) in subsequent steps.

In some embodiments, the method of forming the synthetic bone material may be automated. Automating at least a portion of the method may reduce costs associated with the production of the synthetic bone material. By way of example, the mixing of the calcium oxide and the calcium oxide and phosphorus pentoxide measuring and mixing may be automated. An automated system may be used to provide the ignition source to the mixture. The formation of pellets may be automated. The addition of the dopant may be automated. One or more steps may be automated without deviating from the invention.

Another aspect of the invention is a biomimetic synthetic bone graft material. The synthetic bone graft material includes calcium phosphate. In some embodiments, the synthetic bone graft material may include a dopant. The dopant may be an atom, an ion, a molecule, a compound, or combinations thereof. In some embodiments, the dopant can be strontium or SrO. In some embodiments, the dopant may be magnesium or MgO. In still other embodiments, the dopant may be TCP or hydroxyapatite ("HA"). By way of non-limiting example, in some embodiments, the dopant may be an antimicrobial agent such as silver, gold, copper, zinc, silver nitrate or combinations thereof. In some embodiments, the antimicrobial agent may be silver (Ag) in the metallic or ion state. The antimicrobial agent may be an atom, an ion, a molecule, or a compound. By way of non-limiting example, in some embodiments, the antimicrobial agent may be silver, gold, copper, zinc, silver nitrate or combinations thereof. By way of example, the chemical reaction occurring when silver is selected as the antimicrobial agent is illustrated in Equation 6:

$$3CaO + P_2O_5 + Ag \rightarrow Ca_3(PO_4)_2 + Ag \qquad (6)$$

In some embodiments, the synthetic bone graft material can include hydroxyapatite and tricalcium phosphate. In some embodiments, the synthetic bone graft material comprises about 100% calcium phosphate. In some embodiments where a dopant has been used, the dopant element may be substituted into either the calcium vacancies in the apatite lattice or substitutes for calcium ions. The calcium phosphate may contain different phases of calcium phosphate, for example hydroxyapatite and/or tricalcium phosphate. The phase of calcium phosphate that may be in the synthetic bone graft may affect the solubility and mechanical properties of the synthetic bone graft. In some embodiments, between about 0% to about 100% by weight of the calcium phosphate in the synthetic bone graft material may be hydroxyapatite. In some embodiments, between about 0% to about 100% by weight of the calcium phosphate in the synthetic bone graft material may be β-tricalcium phosphate. In some embodiments, between about 0% to about 100% by weight of the calcium phosphate in the synthetic bone graft material may be α-tricalcium phosphate.

The antimicrobial agent may be locally released into a patient near the implantation site. The rate of antimicrobial agent released from the implant may be a function of the infection. The antimicrobial agent may be released over a period between about hours to years after implantation. The duration of release and the release rate may be dependent upon the starting concentration of the antimicrobial agent in the product. The release rate may also be a function of the phase of calcium phosphate in the synthetic bone graft material as well as the porous structure of the synthetic bone graft material.

An additive material can be combined with the CaP products. The additive material can be added following the heat treatment or may be added to products that have not been heat treated. The additive material can be collagen, immunofluorescence label, alginate, chitosan coatings, BMPs, VEGF, allograft or xenograft bone or tissue or other proteins or mixtures thereof.

In one embodiment, the synthetic bone material may be joined to at least one other object. The objects may be bones, bone materials, synthetic bone materials, BGSM, metals, alloys, ceramics, oxides, or other materials. By way of example, the synthetic bone material may be used to repair and/or graft bones in remote locations of the body. A laser may be used to initiate a self-propagating reaction that may be used to produce synthetic bone materials to join the ends of bones at a remote, or unexposed, location in the body.

There are a variety of applications for the synthetic bone graft material. Multiple products are envisioned to be derived from this invention, including: orthopedic implants such as inter vertebral spacers, osteotomy wedges, bone scaffolds, and any production process calcium phosphates are needed. The synthetic bone graft material may be used as a large scale, bioresorbable, biocompatible, and bioactive BGSM for treatment of extensive battlefield injuries, accidental injuries, bone defects, craniofacial repair, dental applications as well as additional medical treatments that involve repairing or replacing bone materials that have been removed. The synthetic bone graft material may be suitable BGSM, wherein the fabrication and manufacturing of BGSM can potentially benefit from high purity, low cost materials that may be generated utilizing self-propagating reactions. The synthetic bone graft material may also be used to form scaffolds for tissue, that may be used, for example in ex-vivo reconstructions. In a specific embodiment, the biomimetic bone replacement material can be used for operations such as spinal fusion surgeries. The synthetic bone material can be used as a drug delivery device, as a carrier for growth factors, cells and/or proteins for bone tissue.

Another aspect of the invention is a synthetic porous filter, the porous filter comprising a calcium phosphate, wherein the calcium phosphate is formed by mixing calcium oxide and phosphorus pentoxide to form a mixture, and providing an ignition source to the mixture in an inert atmosphere to form the porous filter. The method to form the filter is similar to the process to form a synthetic bone material. The porous filter may be used to filter a fluid. By way of non-limiting example, the filter may be used to filter arsenic in water, and other contaminates present in agricultural settings, such as in fertilization production and use. The filters may be used to filter arsenic in water, phosphates in agriculture, fluorine from water and the like. Porous filters may include dopants. By way of example, the CaP filter may include dopants and/or additives, such as fluorine, chlorine, iodine, bromine or the like that may be used to filter water. In another embodiment, CaP may be used as a substitute to carbon components that are found in water filters. By way of example, CaP may replace carbon particulates found in packed water filters. The CaP particulates may further be doped with a halogen to increase the purification properties of the filter.

FIG. 1 illustrates a method 100 for producing a synthetic bone graft material. The method may also be used to prepare a porous filter. The calcium oxide 102 and the phosphorous pentoxide 104 are combined to form a mixture 106. The mixture is placed into a mold 108 to form a pellet 110. The pellet 110 is ignited using an ignition source 112. The pellet 110 is combusted, for example through a self-propagation reaction 114, until the pellet 110 is converted to a final product 118.

EXAMPLES

Example 1

Reactant powders CaO (Fisher, 325 mesh, 99.99% pure), and $P_2O_5$ (Fisher, 100 mesh, 99.99% pure), were combined with an about 3:1 ratio ($CaO:P_2O_5$) molar ratio and about 0.5 weight % silver, about 1 weight % silver or 2 weight % silver (CERAC, 325 mesh, 99.99%) in a vibrational mixer (LABRAM™) for about 1 minute. Due to the hygroscopic and reactive nature of $P_2O_5$, powders were prepared in a desiccated argon atmosphere. Pellets with dimensions of φ=about 3 in, h=about 3 in, w=about 500 g were pressed and subsequently reacted with a hot press (ENERPAC™) in argon environment. Post-synthesis the pellets were air cooled to room temperature, photographed, and analytically characterized via Scanning Electron Microscopy (SEM) and X-Ray Diffraction (XRD).

Figure 8:
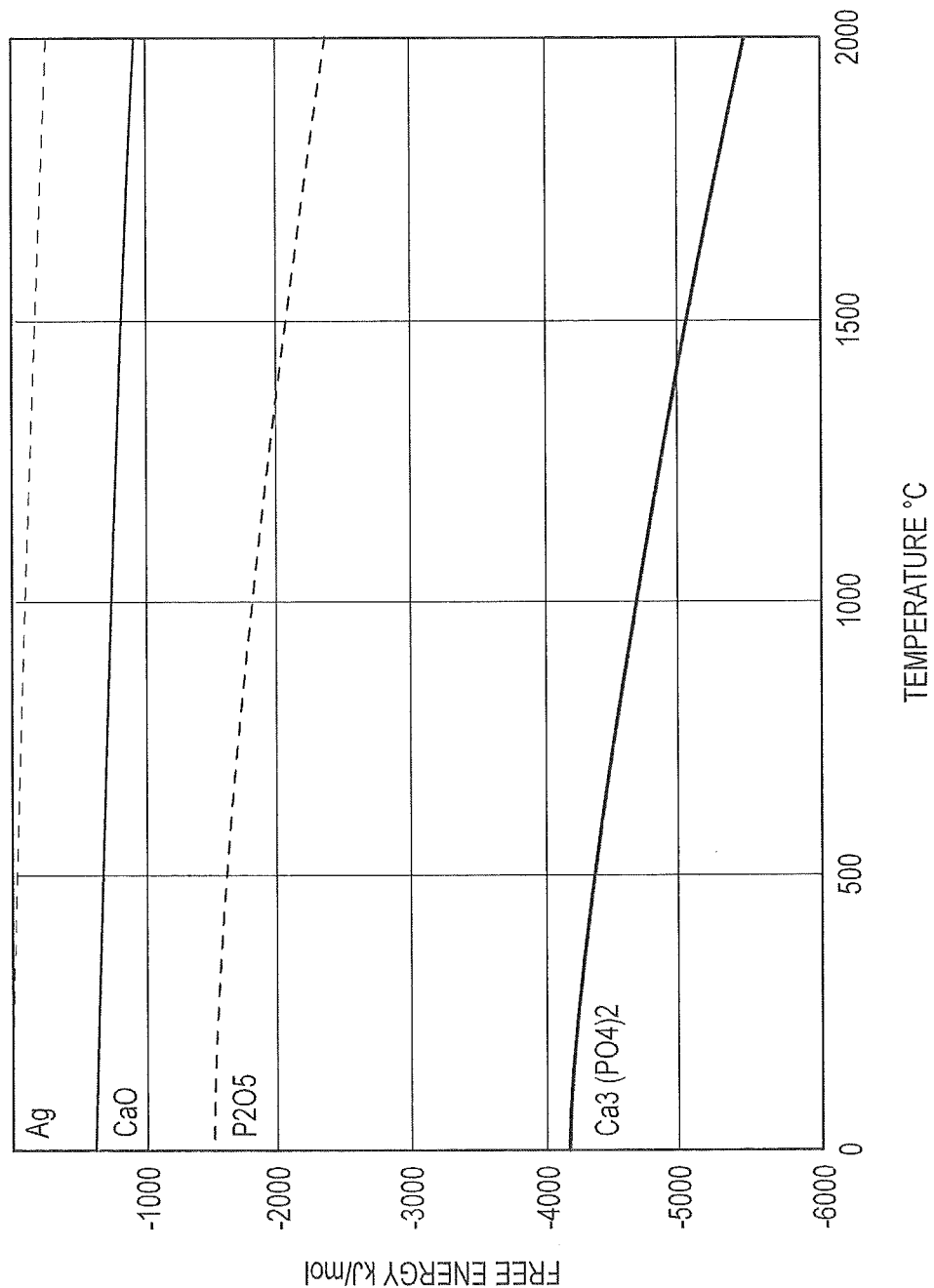
FIG. 8 illustrates a Temperature-Free Energy plot.
Figure 9:
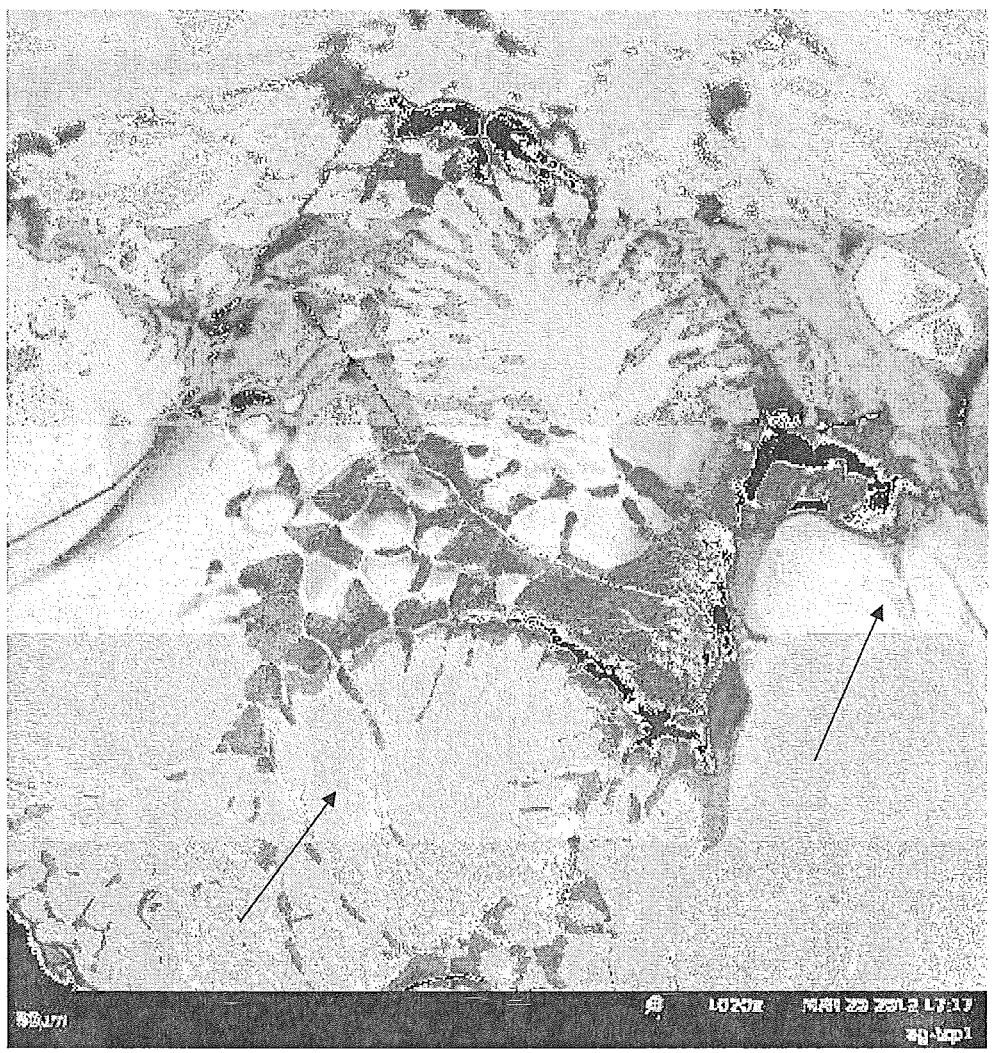
FIG. 9 illustrates a backscatter SEM depicting regions where silver has been incorporated into the CaP microstructure.

A thermochemical assessment of the modified system was performed using HSC Chemistry 5.1 (Outotec©). FIG. 8 illustrates a Temperature-Free Energy plot illustrating that calcium phosphate had the lowest free energy and is therefore the most likely product to form. FIG. 9 illustrates a backscatter SEM illustrating regions where silver has been incorporated into the CaP microstructure.

Figure 2:
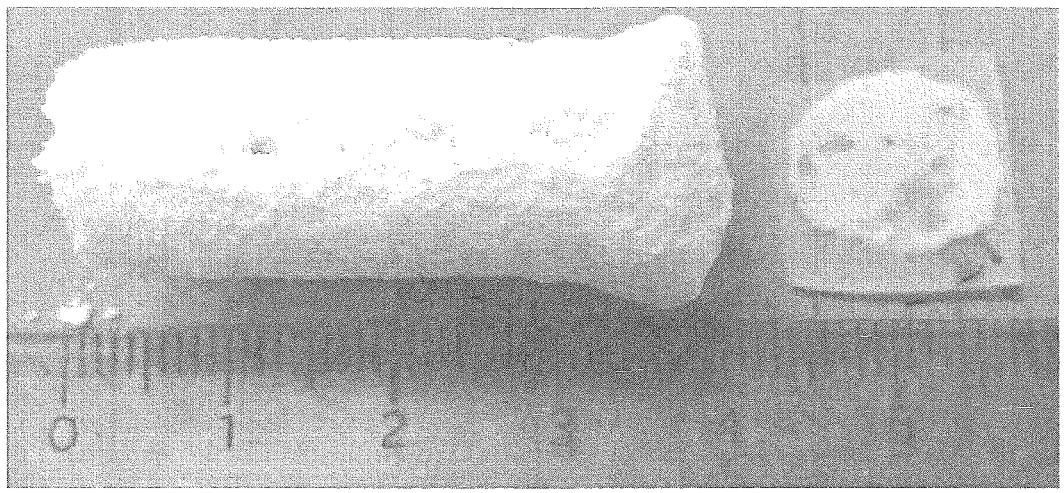
FIG. 2 illustrates a calcium phosphate block that weighs approximately 5 grams.
Figure 3:
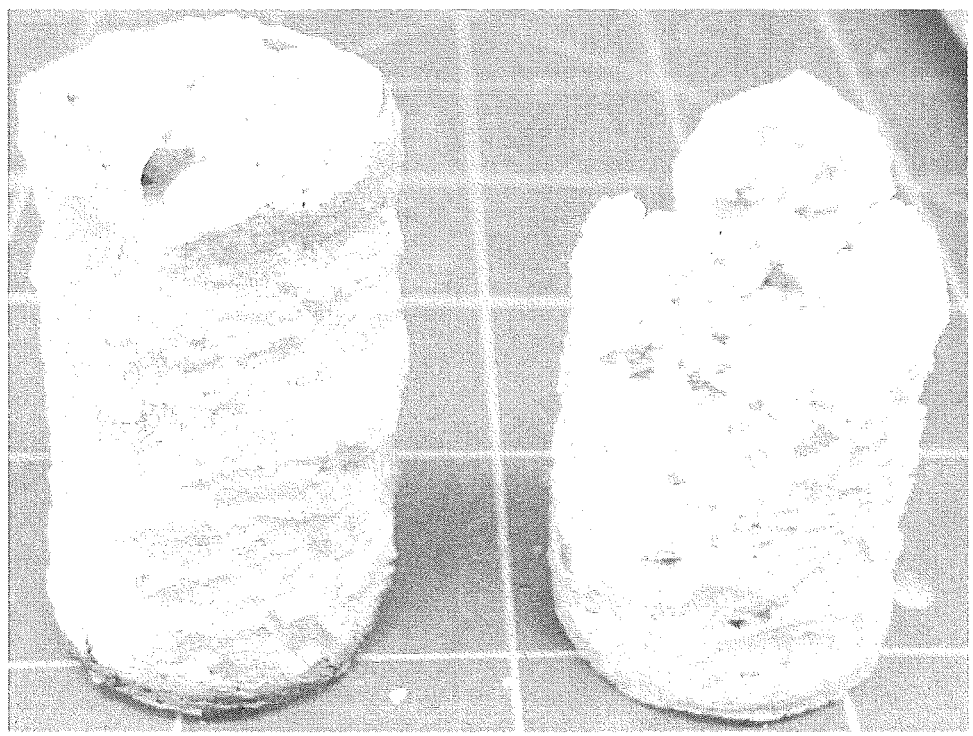
FIG. 3 illustrates a calcium phosphate block approximately 50 grams in weight.

Bulk calcium phosphate blocks doped with about 0.5, about 1 or about 2 weight % silver were successfully prepared using the disclosed self-propagating reaction Eq. 6. FIG. 2 illustrates photographs of as-synthesized calcium phosphate block weighing about 5 g and sectioned pellet (top right). FIG. 3 illustrates a calcium phosphate block weighing about 50 g.

Figure 4:
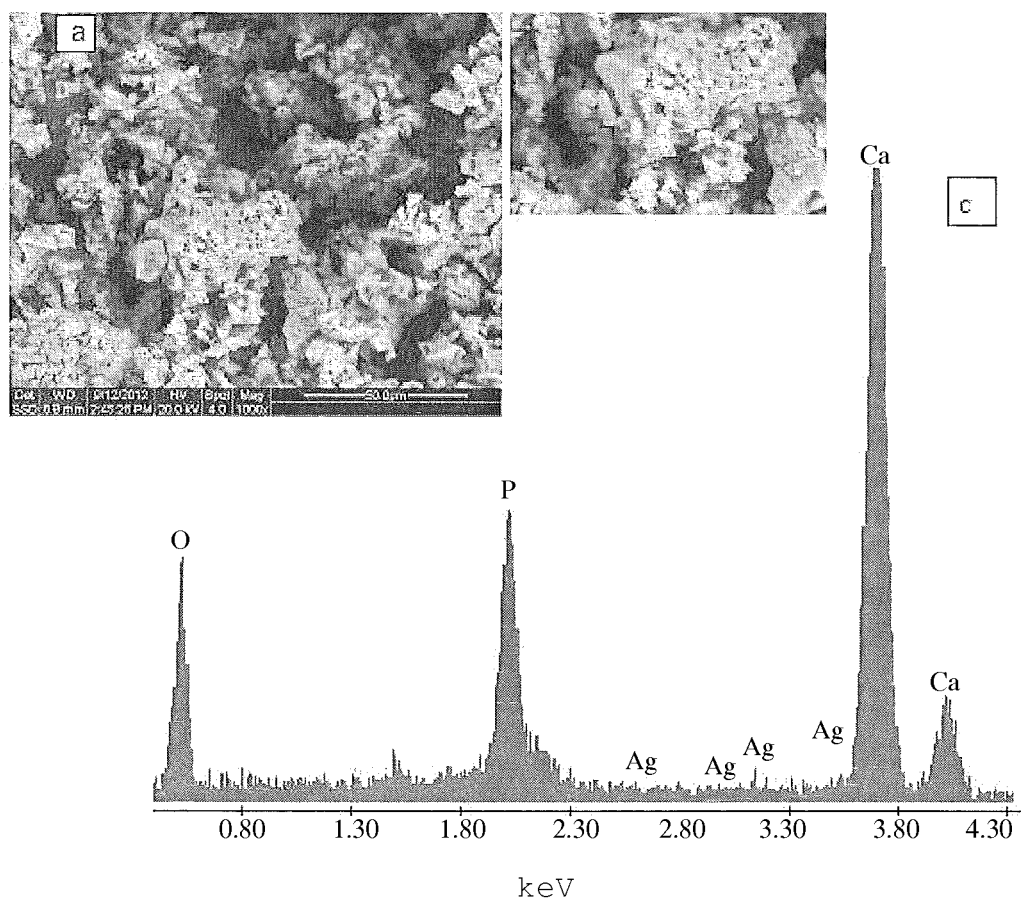
FIG. 4 illustrates backscatter scanning electron micrographs (SEM) for samples substituted with silver ions and an energy dispersive X-ray spectroscopy spectrum.

FIG. 4(a) and FIG. 4(b) illustrate backscatter scanning electron micrographs (SEM) for samples where silver ions are incorporated (arrows) in the calcium phosphate microstructure. FIG. 4 (c) illustrates energy dispersive X-ray spectroscopy (EDAX) and confirms the presence of Ca, P, Ag, O, and C in the constructs.

Figure 5:
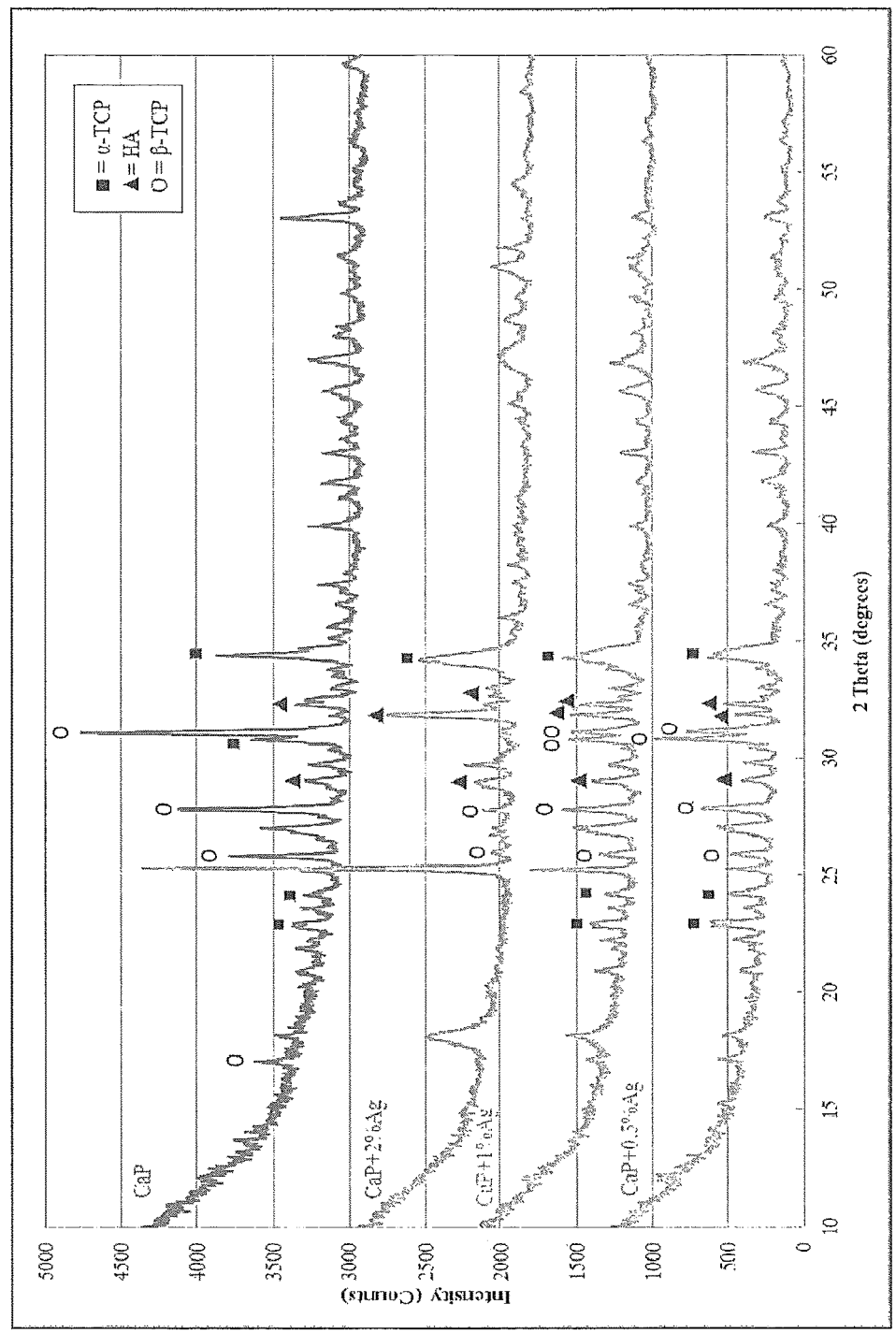
FIG. 5 illustrates powder X-ray diffraction patterns of the calcium phosphates with varying amounts of included silver.

FIG. 5 illustrates powder X-ray diffraction patterns of the calcium phosphates with varying amounts of included silver (Ag), from no silver to about 2% silver. The diffraction patterns indicate HA, α-TCP and β-TCP are present in all samples, and that silver is present three of the samples. There is slight overlap between the Ag and HA and α-TCP peaks. FIG. 5 also illustrates that the concentration of TCP and/or HA may be altered as a function of the amount of silver dopant that was added.

Figure 6:
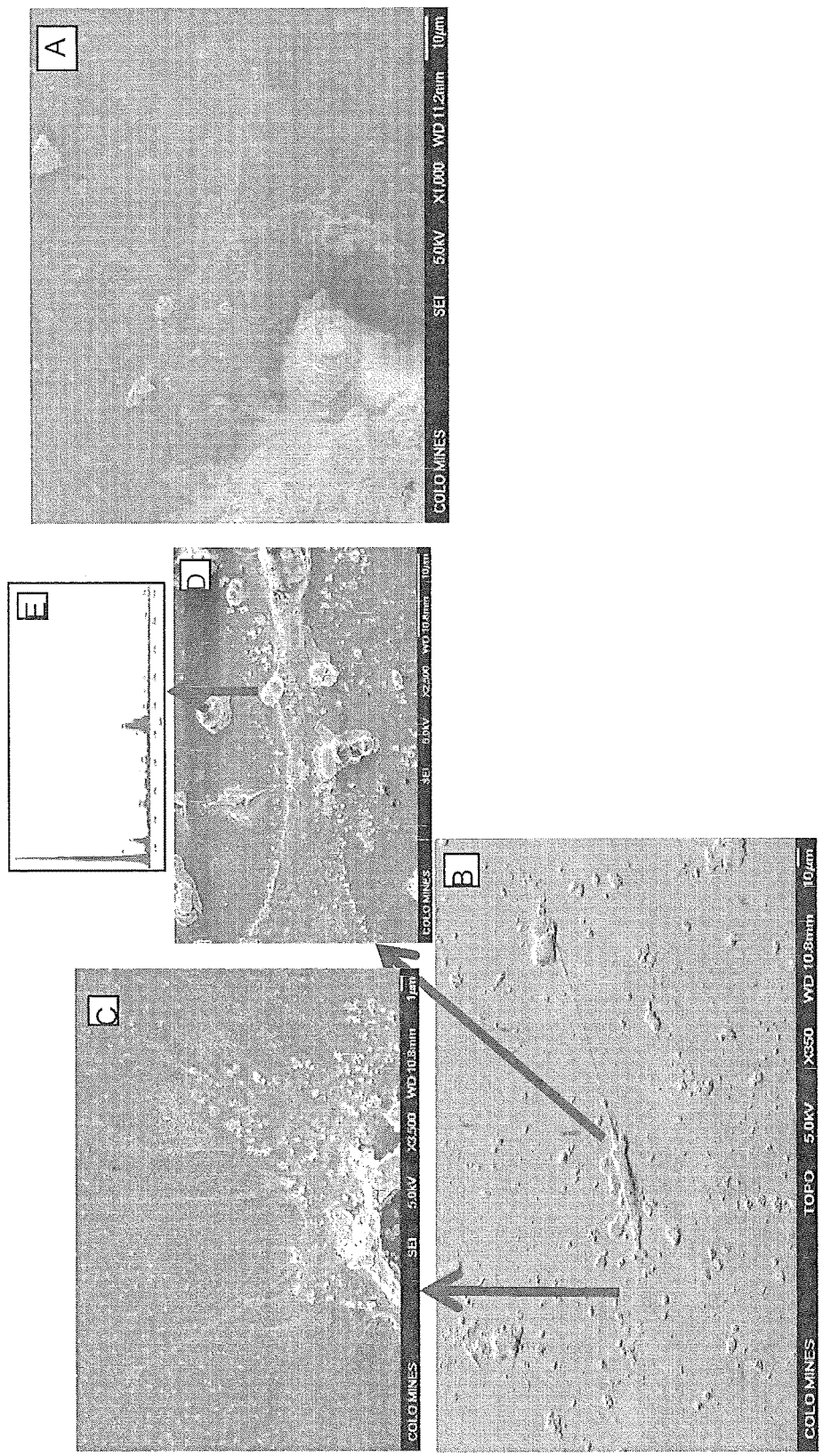
FIG. 6 (A-D) illustrate field emission scanning electron micrographs of cell culture with human fetal osteoblast cell line (hFOB1;19) (CRL-11372 ATCC) and powder for different morphologies and an energy dispersive x-ray.

FIG. 6 (A-D) illustrate scanning electron micrographs of cell culture with human fetal osteoblast cell line (hFOB1.19) (CRL-11372 ATCC), about 10 µg/ml product powder and about 1×10⁵ cells/ml, tracked at days 1, 4 and 7. The powders were not cytotoxic. FIG. 6 further illustrates that cells grew around particles (A) and displayed elongated morphology indicative of healthy cells (B, C). The cells formed matrix vesicles (D, spherical nodules). FIG. 6(E) depicts an energy dispersive x-ray analysis of a spheroid indicated in FIG. 6(D) which demonstrates the presence of calcium and phosphate.

Figure 7:
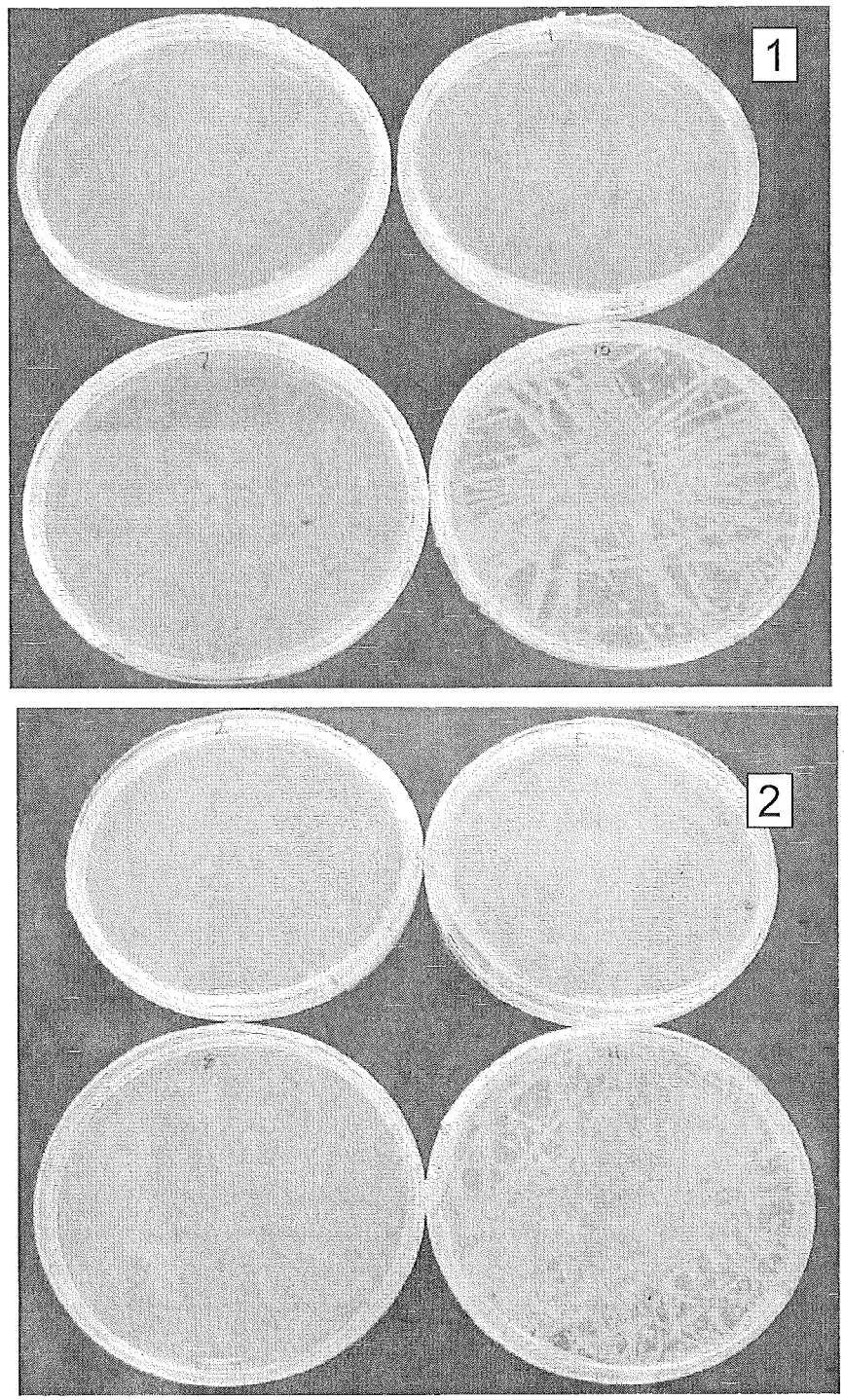
FIG. 7 illustrates photographs of spread plate method with *Escherichia coli* for different samples.

FIG. 7 illustrates photographs of spread plate method with *Escherichia coli* (BAA-1025 ATCC) 10 µg/ml calcium phosphate+Ag powder, about 1×10⁵ cells/ml, after about 24 hours FIG. 7(1), and after about 48 hours FIG. 7(2). The complete inhibition of bacterial growth is evident in all plates except the control (bottom right), for both FIGS. 7(1) and FIGS. 7(2).

Example 2

Synthetic bone graft materials were prepared in accordance with the invention. Products were characterized to determine phases and porosity characteristics through X-ray diffraction, scanning electron microscopy and Fourier transform infrared spectroscopy. Collagen attachment and immunofluorescence labeling were performed to determine which post synthesis heat treatment displayed the highest potential for collagen binding. Results from characterization showed 100% β-TCP in heat treatments of about 1100° C. and about 1150° C. and about 20% α-TCP and about 80% β-TCP in heat treatments of about 1200° C. and about 1250° C. Porosity amongst heat treatments appeared to be consistent and remained about 40±7.8%. A bimodal distribution in pore diameter was found with micropores ranging from about 4 μm to about 12 μm and macropores ranging from about 200 μm to about 4000 μm. Type I collagen attachment at room temperature under agitation was the most effective method to cold mounted and sectioned surfaces of tricalcium phosphate. Other methods included attachment at room temperature and attachment at about 4° C. Collagen attachment increased with increases in specimen heat treatment temperatures. Specimens of approximately 5:1β to α-TCP had the highest attachment.

Figure 10:
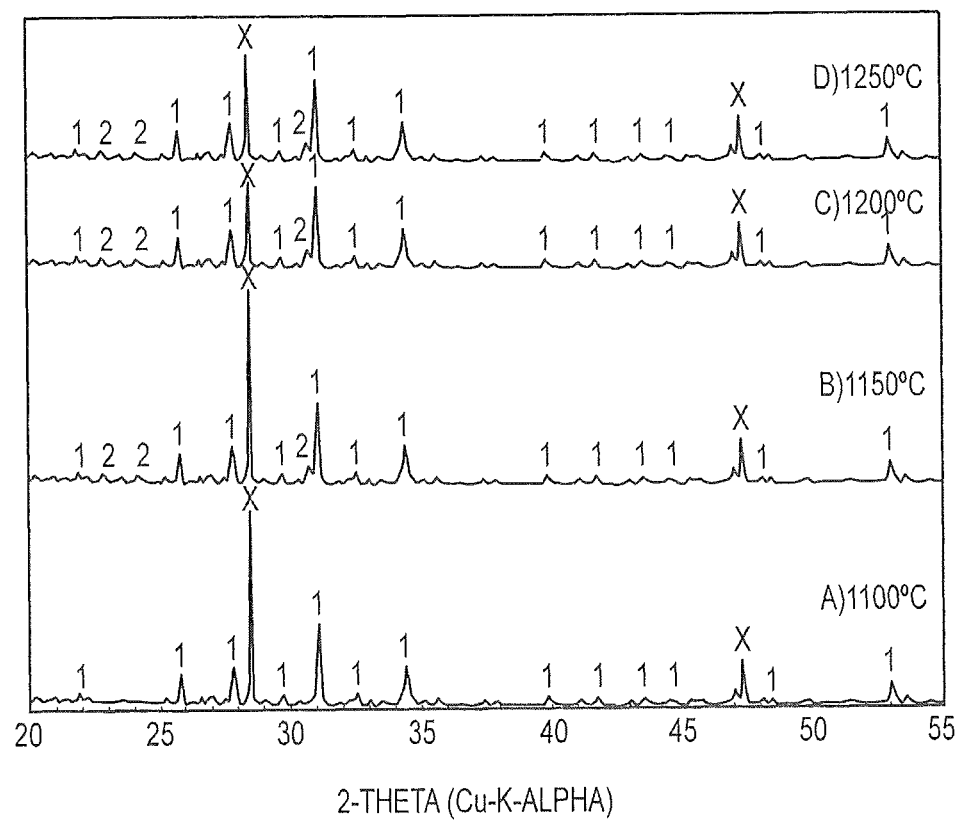
FIG. 10 illustrates a x-ray diffraction pattern for heat treatments.

The two phases found to be present in TCP products were α-TCP and β-TCP. Lower temperature heat treatments of about 1100° C. and about 1150° C. contained peaks that indicated only β-TCP. When the heat treat temperature was increased to about 1200° C. and about 1250° C., a composition of about 20% α-TCP and about 80% β-TCP was present. The representative XRD spectra for samples that underwent the four heat treatments were illustrated in FIG. 10. Peak X indicates Si, peaks marked with "1" indicate β-TCP, while peaks marked with "2" indicate α-TCP.

In addition to the formation of the α-TCP phase at higher treatments, there is a slight left shift in all peaks as heat treatment is increased due most likely to reduction in residual stresses as hexagonal β-TCP begins transformation into monoclinic α-TCP resulting in a volume change.

Figure 11:
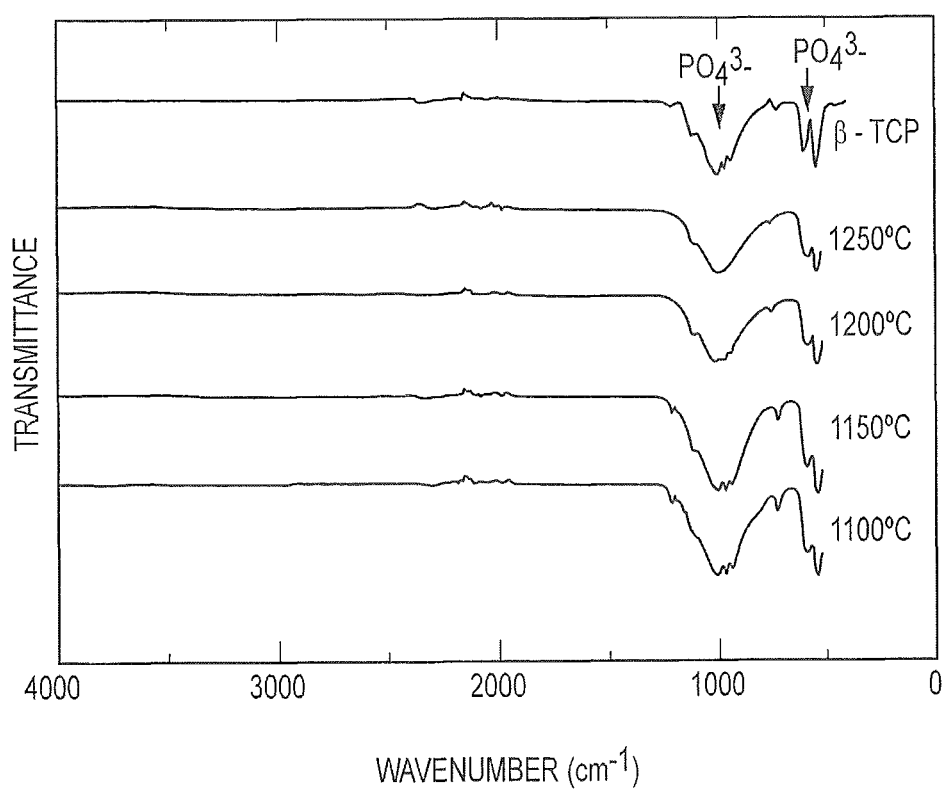
FIG. 11 illustrates transmittance data for heat treated samples and an industry standard β-TCP.

Both phases that comprise the samples, α-TCP and β-TCP, contain the same phosphate bonds. Transmittance data for the heat treated samples were graphed with an industry standard of the β-TCP as illustrated in FIG. 11.

Figure 12:
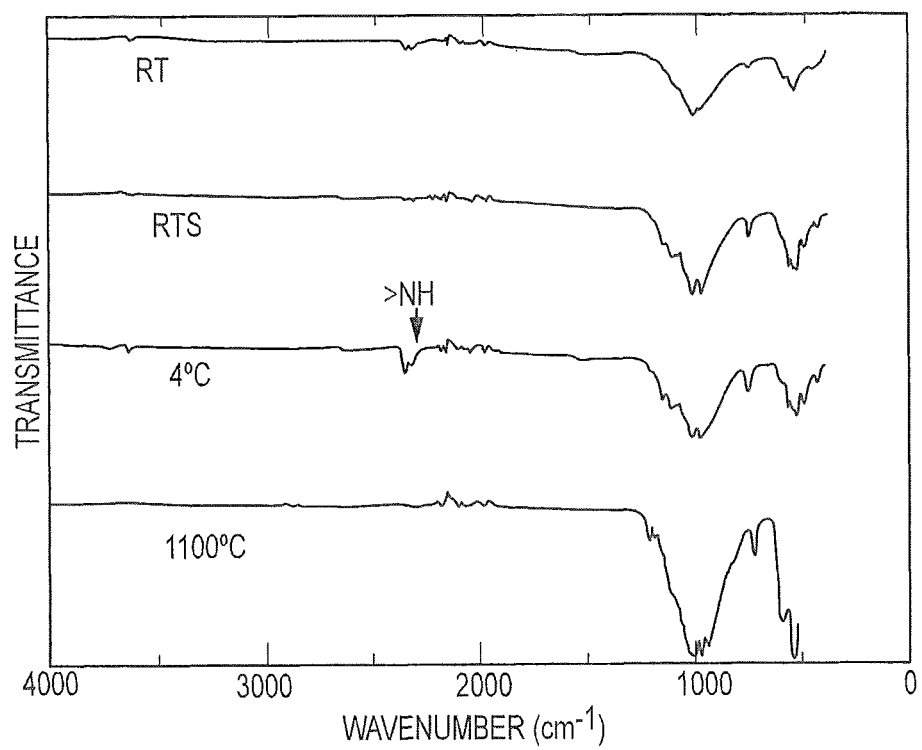
FIG. 12 illustrates collagen bound samples with the transmittance data from the heat treated sample.

The phase peaks at wavenumbers of about 1000 and about 550 were the transmittance regions of $PO_4^{3-}$. As the heat treatment temperature increased over about 1150° C., a smoothing of the transmittance peaks occurred. This curve smoothing is most likely due to the residual stress loss previously described. FIG. 12 illustrates samples with different collagen attachment methods to the sample heat treated at about 1100° C. A peak formed at a wavenumber of about 2400 for the curve treated at about 4° C., which is the range of wavelength in which the nitrogen bond in collagen absorbs light.

Figure 13:
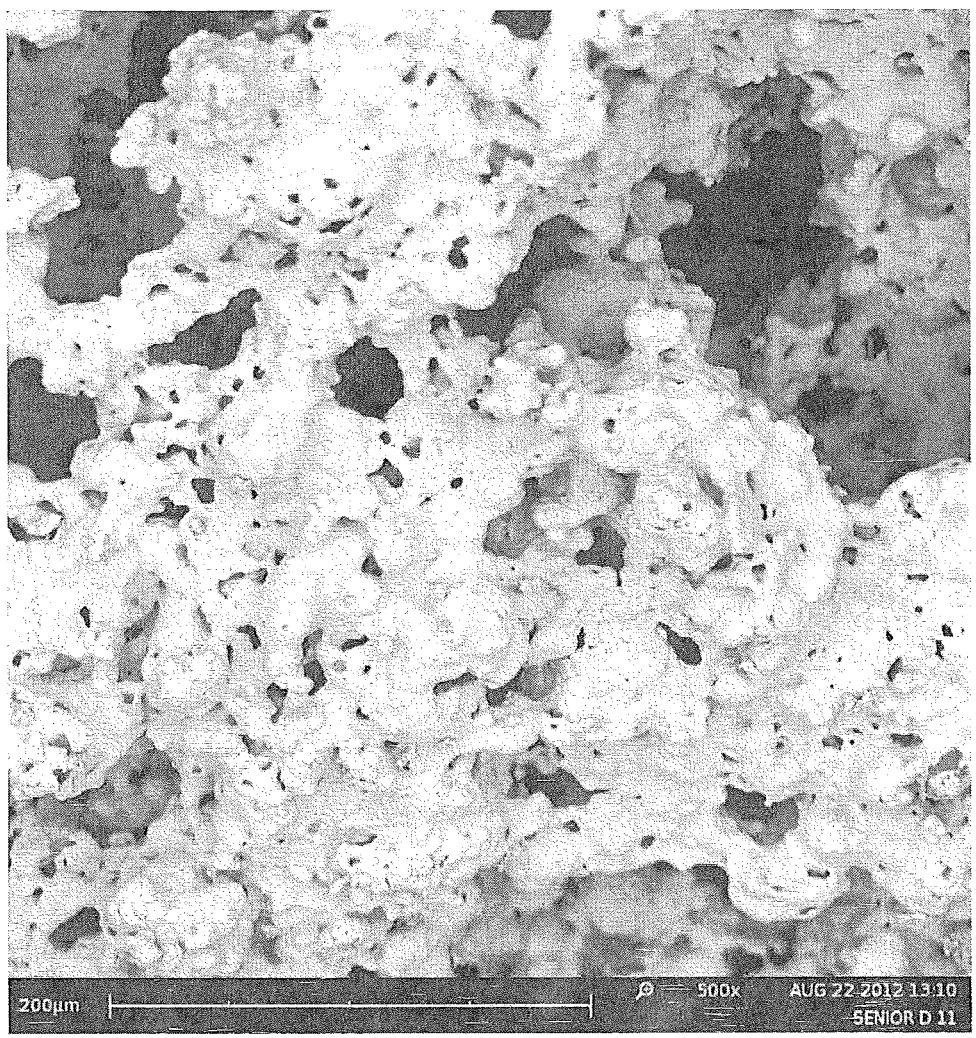
FIG. 13 illustrates an SEM image of a TCP pellet at 500× magnification.

The average porosity of the scaffolds was about 40±7.8%. A representative image of a SEM photo is illustrated in FIG. 13. FIG. 13 illustrates the area and circularity of the pores at about 500× magnification.

Figure 14:
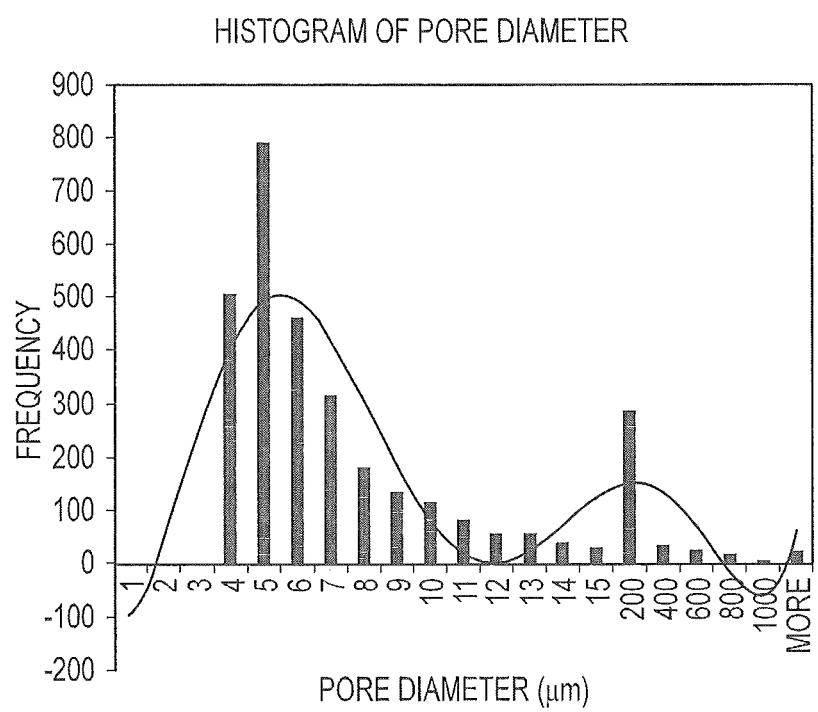
FIG. 14 illustrates the pore diameter versus frequency for pore size determined from SEM images.

FIG. 14 illustrates the bimodal distribution of pore diameter present in TCP samples. The majority of the micropores are between about 4 μm to about 8 μm in diameter and the majority of the macropores are between about 200 μm and about 4000 μm. From the analysis of all the SEM images, it was discovered that porosity was not affected by the heat treatments.

Figure 15:
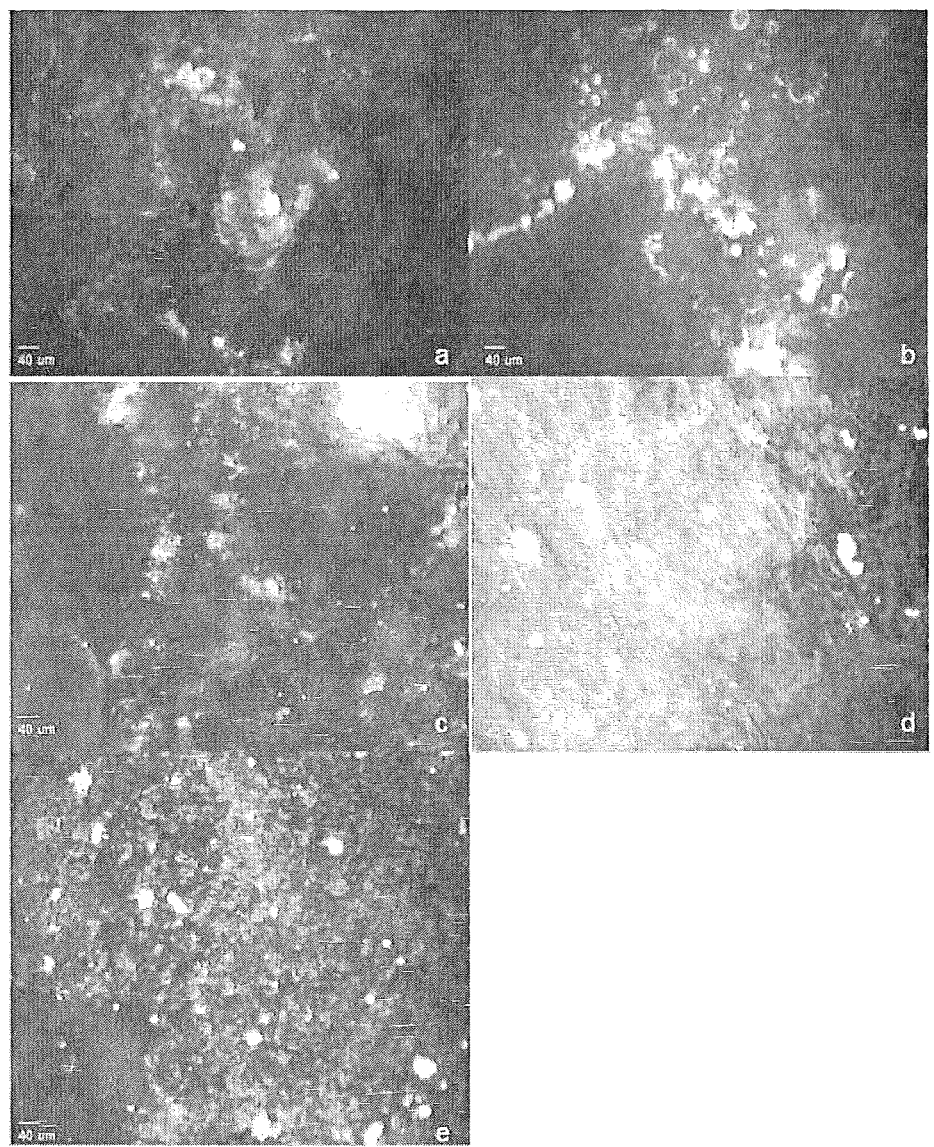
FIG. 15 illustrates representative collagen protein binding to calcium phosphate specimens of various heat treatments.

FIG. 15 illustrates representative collagen protein binding to calcium phosphate specimens of various heat treatments. Supersaturated, bright areas represent regions of collagen attachment because the secondary antibody applied during immunofluorescence labeling re-emits light upon light excitation of the FITC fluorophore. The biocompatibility of TCP was tested through collagen attachment. FIG. 15(a) illustrates a sample that was not heat treated. FIG. 15(b) illustrates a sample that was heat treated at about 1100° C. FIG. 15(c) illustrates a sample that was heat treated at about 1150° C. FIG. 15(d) illustrates a sample that was heat treated at about 1200° C. FIG. 15(e) illustrates a sample that was heat treated at about 1250° C. Type I collagen attached to TCP of every heat treatment as well as samples which were not heat treated under the three following attachment conditions: attaching at about 4° C., attaching at room temperature, and attaching at room temperature on a cell culture shaker. The appearance of fibrils at high magnifications supports the observation that supersaturated areas of immunofluorescence imaging represent regions of Type I collagen attachment. This may be due to the natural tendency of collagen to form elongated fibrils. Imaging the control samples (no collagen treatment) further supports that collagen attachment occurred on TCP surfaces by showing a distinct lack of fluorescence. The percent collagen attachment increased with an increase in heat treatment. The most effective method tested for collagen attachment was allowing collagen to bind to TCP specimen surfaces at room temperature on a shaker. The least effective method was allowing binding at about 4° C. in a refrigerator.

Figure 16:
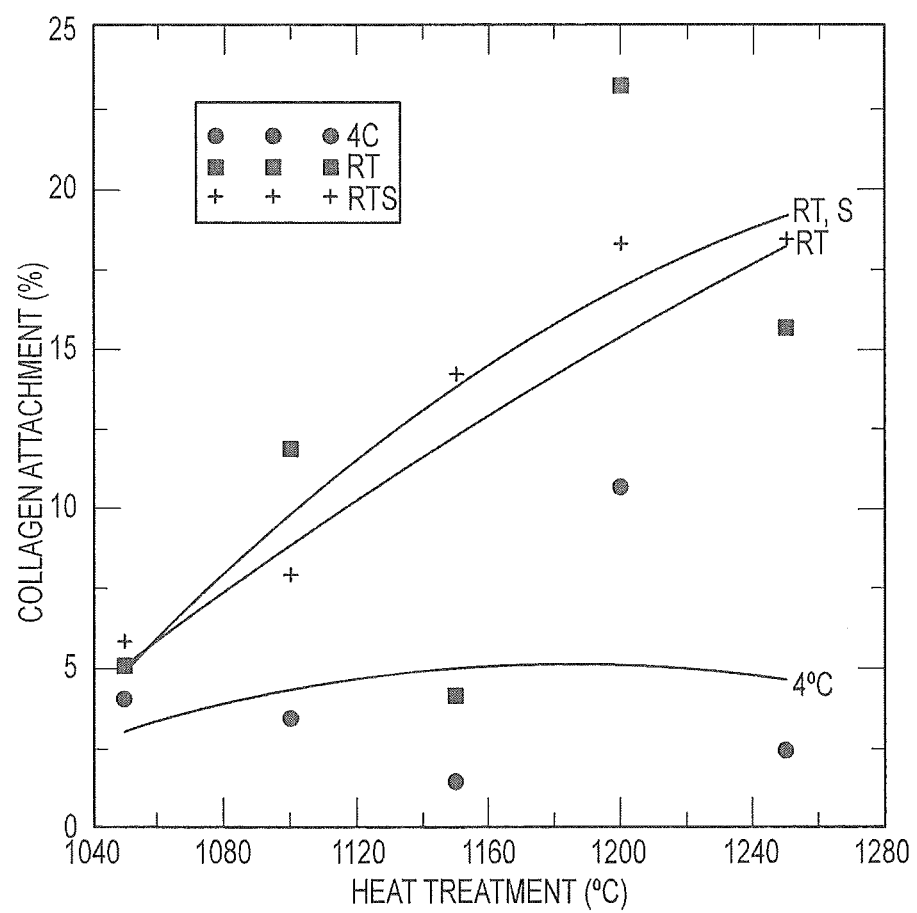
FIG. 16 illustrates threshold analysis of representative collagen protein binding to calcium phosphate specimens.

FIG. 16 illustrates threshold analysis of representative collagen protein binding to calcium phosphate specimens.

The average porosity of constructs was about 40±7.8% which, while low is suitable for mimicking bone structure and potentially allowing bony in growth during vertebral fusion. Given that spongy bone porosity ranges from about 50% to about 90% allowing for cellular influx and tissue ingrowth. Studies show cell behavior depends strongly on the pore dimensions and the interconnectivity of the material. Pore size is also important for the scaffolds to be biocompatible. Micropores in constructs are the correct size to aid in cell movement and attachment as well as in protein and collagen attachment. Macropore sizes are the correct size to aid in larger cellular movement and tissue attachment. Pore diameters and porosity of constructs both demonstrate promising characteristics for in vivo applications.

Collagen attachment proved successful at all heat treatments but showed preferential attachment to higher heat treated samples with shaking attachment. This preference may be attributed to the movement allowing the collagen more opportunities to bind to different sites on the specimens. Also, higher percentages of α-TCP at higher temperatures appear to promote better collagen attachment proving that biphasic materials should be more promising in vivo. Collagen attachment promotes cellular adhesion and successful collagen attachment implies that TCP constructs would be suitable for cellular attachment and biocompatibility testing. Furthermore, this approach can be applied to any protein that has a calcium or phosphate binding affinity.

The foregoing description of the invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the invention. The embodiments described hereinabove are further intended to explain the best mode known for practicing the invention and to enable others skilled in the art to utilize the invention in such, or other, embodiments and with various modifications required by the particular applications or uses of the invention. It is intended that the appended claims be construed to include alternative embodiments to the extent permitted by the prior art.

What is claimed is:

1. A method of producing a synthetic bone graft material, comprising:
   mixing a calcium source and a phosphorus source to form a mixture, wherein the calcium source is selected from the group consisting of calcium oxide, calcium carbonate, calcium hydroxide, calcium fluoride, calcium nitrate, and combinations thereof, and wherein the phosphate source is selected from the group consisting of phosphorous pentoxide, phosphate ($PO_4^{3-}$), pyrophosphate, compounds thereof, and combinations thereof;
   forming the mixture into a pellet: and providing an ignition source to the pellet in an inert atmosphere to form the synthetic bone graft material, wherein an ignition temperature is less than about 100° C.

2. The method of claim 1, wherein a material of the synthetic bone graft material comprises at least one calcium orthophosphate.

3. The method of claim 1, wherein the mixture comprises:
   between about 0.5 to about 0.6 parts of the calcium source; and
   between about 0.4 to about 0.5 parts of the phosphorous source.

4. The method of claim 1, wherein a ratio of the calcium source to phosphorous source in the mixture is about 0.54: about 0.46.

5. The method of claim 1, wherein the mixing occurs in air.

6. The method of claim 1, wherein the mixing occurs in an inert environment, and wherein an inert gas of the inert environment is selected from the group consisting of argon, nitrogen, helium, and combinations thereof.

7. The method of claim 1, further comprising at least one additive of collagen, immunofluorescence label, alginate, chitosan coatings, BMPs, VEGF, allograft bone, xenograft bone, tissue and protein.

8. The method of claim 1, wherein the ignition source is at least one of a laser, a hot wire, an oven, a furnace, a flame, a torch, Joule heating, a hot press, a chemical catalyst, a chemical reaction and combinations thereof.

9. The method of claim 1, wherein the calcium source is a powder.

10. The method of claim 1, wherein the phosphate source is a powder.

11. The method of claim 1, wherein the calcium source is the calcium oxide, and wherein the phosphorus source is the phosphorous pentoxide.

12. The method of claim 1, further comprising heating the synthetic bone graft material at a temperature of between about 25° C. and 1300° C.

13. The method of claim 1, wherein a force applied to the mixture to form the pellet is between about 1 psi and about 80 psi.

14. The method of claim 1, wherein the mixture is pressed into a mold to form the pellet.

15. The method of claim 14, wherein a load of less than about 5000 metric tons of pressure is applied to the mold.

16. The method of claim 1, further comprising mixing the mixture with a dopant.

17. The method of claim 16, wherein the dopant is at least one of Mg, Sr, Sn, silver, gold, copper, zinc, and silver nitrate.

18. The method of claim 16, wherein the dopant is an antimicrobial agent.

19. The method of claim 1, further comprising mixing the calcium source and the phosphorous source with a dopant in an inert environment.

20. The method of claim 19, wherein the mixture comprises:
   between about 50% by weight and about 60% by weight of the calcium source;
   between about 40% by weight and about 50% by weight of the phosphorous source; and
   between about 0.005% by weight and about 30% by weight of the dopant.

* * * * *